(12) United States Patent
Stevens et al.

(10) Patent No.: US 8,149,401 B2
(45) Date of Patent: Apr. 3, 2012

(54) SYSTEM AND METHOD FOR DISTINGUISHING PARTICLES IN A TRANSIENT FLUID

(75) Inventors: Jed Stevens, Colorado Springs, CO (US); Gregory Sprenger, Colorado Springs, CO (US)

(73) Assignee: Velcon Filters, LLC, Colorado Springs, CO (US)

( * ) Notice: Subject to any disclaimer, the term of this patent is extended or adjusted under 35 U.S.C. 154(b) by 93 days.

(21) Appl. No.: 12/696,673

(22) Filed: Jan. 29, 2010

(65) Prior Publication Data

US 2010/0208263 A1  Aug. 19, 2010

Related U.S. Application Data

(60) Provisional application No. 61/152,330, filed on Feb. 13, 2009.

(51) Int. Cl.
*G01N 15/02* (2006.01)
(52) U.S. Cl. ......................................... 356/335; 356/336
(58) Field of Classification Search .......... 356/335–343, 356/432–444, 39–42, 70, 300; 250/573–575, 250/227.23, 227.11, 257
See application file for complete search history.

(56) References Cited

U.S. PATENT DOCUMENTS

| | | |
|---|---|---|
| 4,547,075 A | 10/1985 | Fei |
| 5,200,064 A | 4/1993 | Russ et al. |
| 5,438,420 A | 8/1995 | Harwick et al. |
| 5,739,916 A | 4/1998 | Englehaupt |
| 5,939,727 A | 8/1999 | Sommer |
| 6,064,480 A | 5/2000 | Mountain |
| 6,466,316 B2 | 10/2002 | Modlin et al. |
| 6,873,716 B1 | 3/2005 | Bowker et al. |
| 7,105,849 B2 | 9/2006 | Prelewitz |
| 7,400,407 B2 | 7/2008 | Ng et al. |
| 2004/0201845 A1* | 10/2004 | Quist et al. ................. 356/338 |
| 2005/0122522 A1 | 6/2005 | Padmanabhan et al. |
| 2008/0105837 A1 | 5/2008 | Mack |

* cited by examiner

*Primary Examiner* — Tri T Ton
(74) *Attorney, Agent, or Firm* — Fraser Clemens Martin & Miller LLC; J. Douglas Miller

(57) ABSTRACT

A method for detecting a presence of a particle in a fluid is disclosed. The method includes the steps of directing a beam of electromagnetic radiation into the transient fluid; providing a sensor to detect an intensity of the radiation after passing through at least a portion of the fluid; generating a data representing the intensity detected by the sensor; and analyzing the data based upon a statistical analysis to detect the presence of a particle in the fluid and determine whether the particle is water or a solid particle.

23 Claims, 2 Drawing Sheets

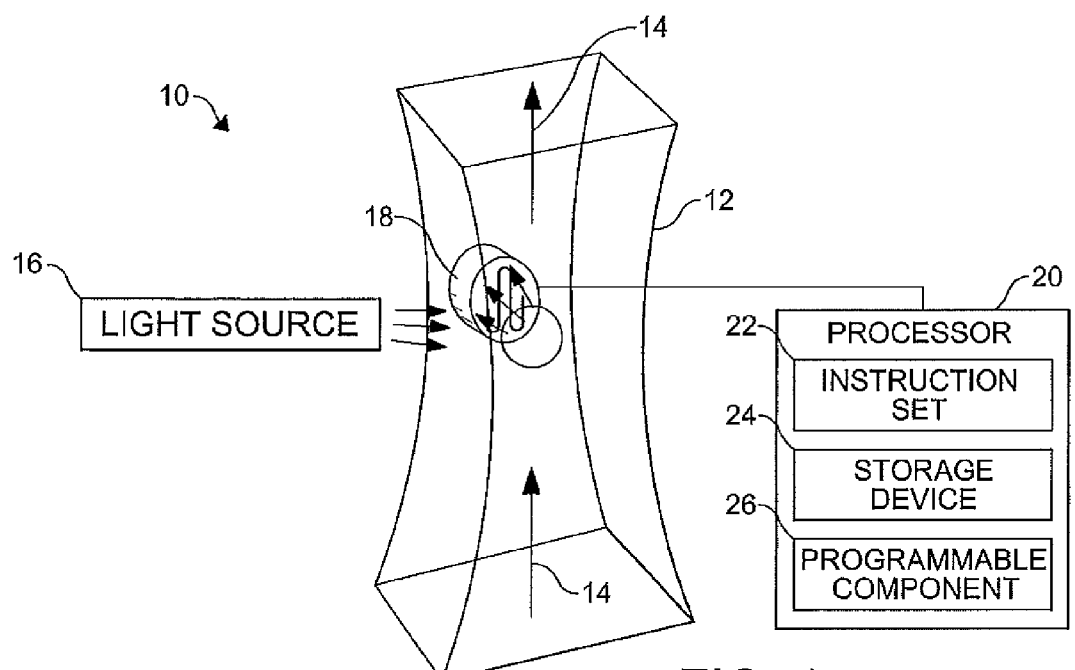
FIG. 1
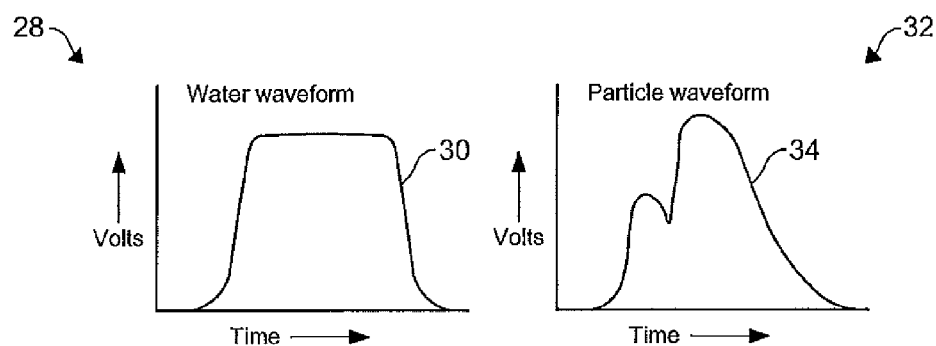
FIG. 2a
FIG. 2b
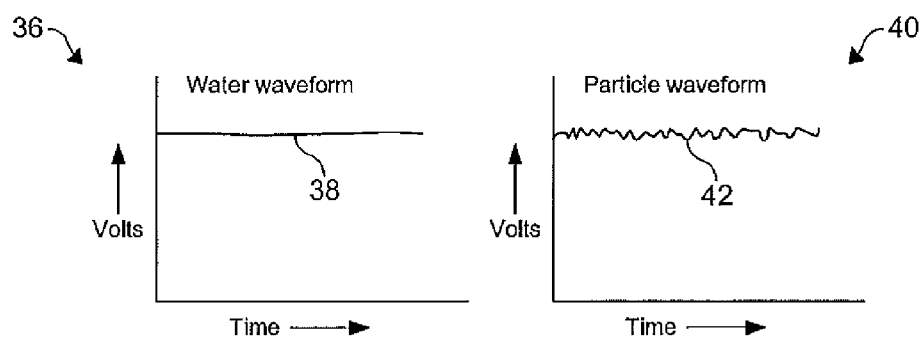
FIG. 3a
FIG. 3b

SYSTEM AND METHOD FOR DISTINGUISHING PARTICLES IN A TRANSIENT FLUID

CROSS-REFERENCE TO RELATED APPLICATION

The present application claims the benefit of U.S. Provisional Patent Application Ser. No. 61/152,330 filed on Feb. 13, 2009, hereby incorporated herein by reference in its entirety.

FIELD OF THE INVENTION

The invention relates to particle sensing instruments for fluids. More particularly, the invention is directed to a sensing system and a method for distinguishing between water and a solid particle in a transient fluid.

BACKGROUND OF THE INVENTION

Particle-sensing and measuring instruments have been available for many years. A particular problem with current particle sensing and measuring instruments is distinguishing between water and solid particles. The distinction between water and various solids is important in a variety of applications, especially where both water and solid particles are likely to be present in a transient fluid to be tested. For example, in the case of contamination of jet fuel, cleanliness requirements are different for solid particles versus water. Typically, the allowable limits for water are an order of magnitude higher than those for solid particles.

It would be desirable to develop a sensing system and a method for distinguishing between water and a solid particle in a transient fluid, wherein the system and method provide a statistical analysis for an individual particle or particle collection to determine whether the particle is a solid or water.

SUMMARY OF THE INVENTION

Concordant and consistent with the present invention, a sensing system and a method for distinguishing between water and a solid particulate in a transient fluid, wherein the system and method provide a statistical analysis for an individual particle or particle collection to determine whether the particle is a solid or water, has surprisingly been discovered.

Solid particulates and water each provide distinct optical effects in the presence of electromagnetic radiation (e.g. light). A water particulate, being generally smooth and spherical, generates no significant optical change as the water tumbles and moves in a transient fluid. A water particulate is optically identical, independent of its orientation. However, solid particles are typically non-spherical and exhibit a variation in overall physical shape as well as their surface properties, including roughness. The variation in surface texture and shape can be detected optically by examining a variation in light as the solid particle interacts therewith. By examining the interaction of light and various particulates as a function of time, one can conduct statistical analysis in real time to determine whether the particle is a solid or water.

In one embodiment, a sensing system for distinguishing between water and a solid particle in a transient fluid comprises: a channel for directing a flow of the fluid; a light source directing an electromagnetic radiation into the channel; a sensor positioned to measure an intensity of the radiation after passing through at least a portion of the fluid in the channel, wherein the sensor transmits a data representing the intensity measurement; and a processor to receive the transmitted data and analyze the data based upon a statistical analysis to detect the presence of a particle in the fluid and determine whether the particle is water or a solid particle.

The invention also provides methods distinguishing between water and a solid particle in a transient fluid.

One method comprises the steps of: directing a beam of electromagnetic radiation into the transient fluid; providing a sensor to detect an intensity of the radiation after passing through at least a portion of the fluid; generating a data representing the intensity detected by the sensor; and analyzing the data based upon a statistical analysis to detect the presence of a particle in the fluid and determine whether the particle is water or a solid particle.

Another method comprises the steps of: directing a beam of electromagnetic radiation into the transient fluid; providing a sensor to detect an intensity of the radiation after passing through at least a portion of the fluid; generating at least one of a data and a waveform representing the intensity detect by the sensor; and analyzing the at least one of a data and a waveform based upon at least one of a statistical analysis and a waveform analysis in real time to distinguish between water and solid particles in the transient fluid.

BRIEF DESCRIPTION OF THE DRAWINGS

The above, as well as other advantages of the present invention, will become readily apparent to those skilled in the art from the following detailed description of the preferred embodiment when considered in the light of the accompanying drawings in which:

FIG. 1 is a schematic representation of sensing device according to an embodiment of the present invention;

FIG. 2a is a graphical representation of an individual particle sensor output as a water particulate travels through a sensing zone of the device of FIG. 1;

FIG. 2b is a graphical representation of an individual particle sensor output as a solid particulate travels through a sensing zone of the device of FIG. 1;

FIG. 3a is a graphical representation of a particle collection sensor output as a water particulate travels through a sensing zone of the device of FIG. 1;

FIG. 3b is a graphical representation of a particle collection sensor output as a solid particulate travels through a sensing zone of the device of FIG. 1;

DETAILED DESCRIPTION OF EXEMPLARY EMBODIMENTS OF THE INVENTION

Figure 4:
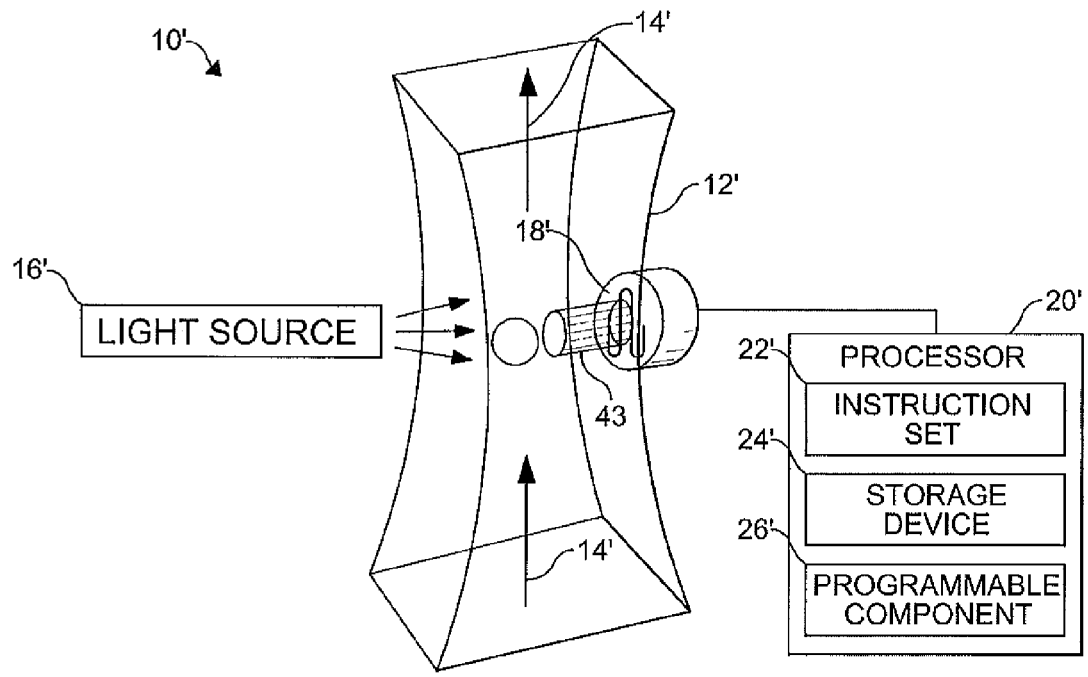
FIG. 4 is a schematic representation of a sensing device according to another embodiment of the present invention.

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

FIG. 1 illustrates a sensing system 10 according to an embodiment of the present invention. The sensing system 10 includes a channel 12 for directing a flow of fluid 14, a light source 16 to direct a beam of electromagnetic radiation through a portion of the channel 12, a sensor 18, and a processor 20.

In the embodiment shown, the channel 12 has a generally hourglass shape having a variable cross sectional area through which the flow of fluid 14 can pass. However, the channel 12 can have any shape or size to direct the flow of fluid 14 in a pre-determined flow path.

The light source 16 is typically a laser for directing a beam of electromagnetic radiation (e.g. light beam) toward the channel 12. However, it is understood that other sources of electromagnetic radiation may be used. In certain embodiments, the beam of electromagnetic radiation is directed through a portion of the channel 12 having the smallest cross-sectional area through which the flow of fluid 14 can pass.

The sensor 18 is typically a light sensor positioned at a pre-determined angle relative to the radiation emitted from the light source 16 to measure an amount of radiation scattered by water or a solid particulate (i.e. particle) disposed in the flow of fluid 14. As a non-limiting example, the sensor 18 measures an intensity of the electromagnetic radiation after passing through at least a portion of the fluid 14 in the channel and transmits an output data representing the intensity measurement.

In certain embodiments, flow velocity (i.e. flow rate) of the fluid 14 is pre-determined to assure that only a single particle (e.g. solid or water) is in a sensing zone of the sensor 18 at one time (i.e. individual particle detection). In certain embodiments, the flow velocity is based upon a known or detected particulate/water concentration in the fluid 14.

In other embodiments, the sensor 18 has a sensing zone with a detection area large enough to sense a plurality of particles simultaneously (i.e. particle collection detection). As a non-limiting example, a turbidimeter can be used. It is understood, that any sensor or light detection device having any size sensing zone can be used.

The processor 20 may be any device or system adapted to receive a data and analyze the data to detect the presence of particle contaminants in the fluid 14 and determine whether the contaminants are water or solid particulates. In certain embodiments, the processor 20 is a micro-computer. In the embodiment shown, the processor 20 receives the data from the sensor 18. It is understood that the processor 20 may be in communication with and may provide control of other devices, systems and components.

As shown, the processor 20 analyzes and evaluates the data based upon an instruction set 22. The instruction set 22, which may be embodied within any computer readable medium, includes processor executable instructions for configuring the processor 20 to perform a variety of tasks. It is understood that the processor 20 may execute a variety functions such as controlling the functions of the light source 16 and the sensor 18, for example. As a non-limiting example, the analysis performed by the processor 20 is based upon at least one of a waveform analysis and a statistical program which compares the light intensity patterns of solid particles to light intensity patterns of water to distinguish therebetween.

In certain embodiments, the processor 20 includes a storage device 24. The storage device 24 may be a single storage device or may be multiple storage devices. Furthermore, the storage device 24 may be a solid state storage system, a magnetic storage system, an optical storage system or any other suitable storage system or device. It is understood that the storage device 24 is adapted to store the instruction set 22. Other data and information may be stored and cataloged in the storage device 24 such as the data collected by the sensor 18, for example.

The processor 20 may further include a programmable component 26. It is understood that the programmable component 26 may be in communication with any other component of the sensing system 10 such as the light source 16 and the sensor 18, for example. In certain embodiments, the programmable component 26 is adapted to manage and control processing functions of the processor 20. Specifically, the programmable component 26 is adapted to modify the instruction set 22 and control the analysis of the data received by the processor 20. It is understood that the programmable component 26 may be adapted to manage and control the light source 16 and the sensor 18. It is further understood that the programmable component 26 may be adapted to store data and information on the storage device 24, and retrieve data and information from the storage device 24.

FIGS. 2a and 2b illustrate non-limiting examples of an output of the sensor 18 adapted for individual particle detection as the flow of fluid 14 passes through the sensing zone thereof. Specifically, FIG. 2a illustrates a graphical representation 28 (voltage v. time) of a water waveform 30. FIG. 2b illustrates a graphical representation 30 (voltage v. time) of a solid particle waveform 34. As shown, the water waveform 30 is generally smooth and symmetrical, while a non-spherical particle generates the solid particle waveform 34 having a jagged and non-symmetrical shape. The variations in shape, symmetry, and standard deviation of the waveforms 30, 34 can be analyzed statistically by the processor 20 to differentiate between water and solid particles. Other statistical analysis can be used such as running mean and variance.

FIGS. 3a and 3b illustrate non-limiting examples of an output of the sensor 18 adapted for particle collection detection as the flow of fluid 14 passes through the sensing zone thereof. Specifically, FIG. 3a illustrates a graphical representation 36 (voltage v. time) of a water waveform 38. FIG. 3b illustrates a graphical representation 40 (voltage v. time) of a solid particles waveform 42. As shown, the water waveform 38 exhibits little variation due to the spherical nature of the water droplets in the flow of fluid 14. Conversely, the non-spherical solid particles exhibit a variation, as illustrated by the solid particles waveform 42. The variations in shape, symmetry, and standard deviation of the waveforms 38, 42 can be analyzed statistically by the processor 20 to differentiate between water and solid particles.

In use, the beam of electromagnetic radiation generated by the light source 16 is directed through the flow of fluid 14 in the channel 12. The sensor 18 is positioned to measure the amount of light scattered by a particle (solid contaminant or water) flowing through a path of the beam. The sensor 18 transmits a data representing a light intensity received thereby as a function of time. The processor 20 receives the data from the sensor 18 to analyze a light intensity pattern of the scattered light. As a non-limiting example, the analysis is performed in real time. As a further non-limiting example, the analysis performed by the processor 20 is based upon at least one of a waveform analysis and a statistical variation program to compare light intensity patterns of solid particles to light intensity patterns of water and determine the state of individual particles or contaminants detected in the transient fluid 14. In certain embodiments, the analysis performed by the processor 20 is statistical analysis including the calculation of at least one of a running mean, a standard deviation, and a variance of the data transmitted by the sensor 18. In certain embodiments, the waveform analysis includes at least one of symmetry analysis, a rise and fall slope, a peak height, and a peak height consistency between the rise and fall. For water, a waveform rise and fall slope is typically identical (one positive and one negative) and the peak height is substantially consistent while the water is in the sensing zone of the sensor 18.

An average light output intensity detected by the sensor 18 is generally an indication of an amount of solid particles and/or water (or an indication of scattering surface area of the particle collection). A variation in the waveforms 30, 34, 38, 42 is typically due to non-spherical particle tumbling as the solid particulate travels through the sensing zone of the sensor 18. It is understood that the light-scattering characteristics of water do not change while the water tumbles. Specifically, the scattered light intensity can be analyzed to properly size the water particle, due to the transparent nature or difference in index of refraction between the water and the fluid 14. In certain embodiments, data received from the sensor 18 is analyzed by the processor 20 to determine a maximum amount of light scattered as a particle flows through the sensing zone. It is understood that a processor 20 may be used to analyze a light intensity received by the sensor 18 or a waveform representing the received light intensities. It is further understood that variation in the light intensities may be analyzed using various statistical methods.

FIG. 4 illustrates a sensing system 10' according to an embodiment of the present invention similar to the sensing system 10 except as described herein below. Structure repeated from the description of FIG. 1 includes the same reference numeral and a prime (') symbol.

As shown, the sensing system 10' is a light-extinction individual particle-detecting device. The sensing system 10' includes a channel 12' for directing a flow of fluid 14', a light source 16' to direct a beam of electromagnetic radiation through a portion of the channel 12', a sensor 18', and a processor 20'.

The light sensor 18' is disposed adjacent the channel 12' opposite the light source 16' to measure a reduction in intensity of the radiation passing through the fluid 14' as particulates (e.g. water and solid particles) pass through the sensing zone of the sensor 18'. In other words, the sensor 18' is adapted to detect a shadow 43 generated by a particulate passing through the beam of radiation emitted by the light source 16'. In certain embodiments, the light intensities detected by the sensor 18' are represented in a waveform.

Figures 5A, 5B:
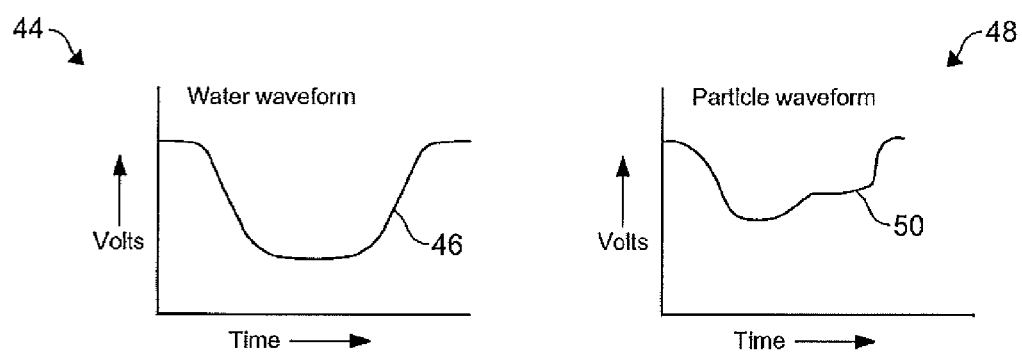
FIG. 5a is a graphical representation of an individual particle sensor output as a water particulate travels through a sensing zone of the device of FIG. 4.
FIG. 5b is a graphical representation of an individual particle sensor output as a solid particulate travels through a sensing zone of the device of FIG. 4.

FIGS. 5a and 5b illustrate non-limiting examples of a waveform output of the sensor 18' adapted for individual particle detection as the flow of fluid 14' passes through the sensing zone thereof. Specifically, FIG. 5a illustrates a graphical representation 44 (voltage v. time) of a water waveform 46. FIG. 5b illustrates a graphical representation 48 (voltage v. time) of a solid particle waveform 50. As shown, the water waveform 46 is generally smooth and symmetrical, while a non-spherical solid particle generates the particle waveform 50 having a jagged and non-symmetrical shape. The variation in shape and peak deviation can be analyzed statistically to differentiate between water and solid particles. As shown in FIGS. 5a and 5b, the typical waveforms 46, 50 of the light-extinction individual particle-detecting device 10' is generally an inverted representation of the waveforms produced by a light scattering device. Specifically, the shadow 43 of water is smooth and symmetrical as the water moves through the sensing zone of the sensor 18'. Conversely, a non-spherical solid particle exhibits a jagged and non-symmetrical light shadow.

The processor 20' analyzes the light output signal variation and determines whether the particle is water or a non-spherical solid particle. A size of the particle can be determined by calculating a maximum light reduction (i.e. maximum drop in voltage) including a pre-determined difference factor for each of water and a solid particulate. It is understood that water may allow a focused beam of radiation to reach the sensor 18', causing the sensor 18' to report an inaccurate size of the water particulate. Accordingly, electronic compensation can be used.

The operation of the sensing system 10' (i.e. light extinction system) is generally the same as the sensing system 10 (i.e. light scattering system). However, the resultant data collected by the sensor 18' is an inverted representation of the data collected by the sensor 18. Accordingly, the received data may be analyzed by the processor 20' based upon a statistical program or waveform analysis adjusted for the inverted data to determine if the particle is water or some other solid particle. As a non-limiting example, the analysis of the output data may include an analysis of data dispersion or inconsistency. Specifically, a data is stored and carried forward as a consistent number of data values. As new data is gathered, earlier data is dropped from the "window" of data. Accordingly, data analysis can include calculation of running means, standard deviation, and variance, for example. It is understood that water generally produces low data inconsistency. It is further understood that variation in the light intensities may be analyzed using various statistical methods.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A method for distinguishing between a water particulate and a solid particulate in a transient fluid, the method comprising the steps of:
   directing a beam of electromagnetic radiation into the transient fluid;
   providing a sensor to detect an intensity of the radiation after passing through at least a portion of the fluid;
   generating a data representing the intensity detected by the sensor; and
   analyzing the data based upon a statistical analysis to detect the presence of a particulate in the transient fluid and to distinguish the particulate between a water particulate and a solid particulate.

2. The method according to claim 1, wherein the beam of electromagnetic radiation is generated by a laser.

3. The method according to claim 1, wherein the sensor is disposed in a pre-determined position relative to a source of the radiation to detect the intensity of a portion of the radiation reflected from the particulate in the fluid.

4. The method according to claim 1, wherein the sensor is disposed adjacent the fluid and opposite a source of the radiation to detect a shadow generated by the particulate in the fluid.

5. The method according to claim 1, wherein the sensor is a particle collection sensor having a sensing zone capable of simultaneously detecting a plurality of the particulates in the fluid.

6. The method according to claim 1, wherein the data represents the sensed light intensity as a function of time.

7. The method according to claim 1, wherein the statistical analysis includes calculating at least one of a running mean, a standard deviation, and a variance.

8. The method according to claim 1, wherein the statistical analysis includes determining at least one of a rise and fall slope, a peak height, and a peak height consistency between a rise and a fall.

9. The method according to claim 1, wherein the statistical analysis includes determining a size of the particulate.

10. A method for distinguishing between a water particulate and a solid particulate in a transient fluid, the method comprising the steps of:
   directing a beam of electromagnetic radiation into the transient fluid;
      providing a sensor to detect an intensity of the radiation after passing through at least a portion of the fluid;
      generating at least one of a data and a waveform representing the intensity detect by the sensor; and
   analyzing at least one of the data and the waveform based upon at least one of a statistical analysis and a waveform analysis in real time to detect the presence of a particulate in the transient fluid and to distinguish the particulate between a water particulate and a solid particulate in the transient fluid.

11. The method according to claim 10, wherein the sensor is disposed in a pre-determined position relative to a source of the radiation to detect the intensity of a portion of the radiation reflected from the particulate in the fluid.

12. The method according to claim 10, wherein the sensor is disposed adjacent the fluid and opposite a source of the radiation to detect a shadow generated by the particulate in the fluid.

13. The method according to claim 10, wherein the sensor is a particle collection sensor having a sensing zone capable of simultaneously detecting a plurality of the particulates in the fluid.

14. The method according to claim 10, wherein the data represents the sensed intensity as a function of time.

15. The method according to claim 10, wherein the statistical analysis includes calculating at least one of a running mean, a standard deviation, and a variance.

16. The method according to claim 10, wherein the waveform analysis includes determining at least one of a rise and fall slope, a peak height, and a peak height consistency between a rise and a fall.

17. A sensing system for distinguishing between a water particulate and a solid particulate in a transient fluid, the system comprising:
   a channel for directing a flow of the fluid;
   a light source directing an electromagnetic radiation into the channel;
   a sensor positioned to measure an intensity of the radiation after passing through at least a portion of the fluid in the channel, wherein the sensor transmits a data representing the intensity measurement; and
   a processor to receive the transmitted data and analyze the data based upon a statistical analysis to detect the presence of a particulate in the transient fluid and to detect the presence of a particulate in the transient fluid and to distinguish the particulate between a water particulate and a solid particulate.

18. The sensing system according to claim 17, wherein the sensor is disposed adjacent the channel in a position to measure a radiation reflected from the particulate in the flow of fluid.

19. The sensing system according to claim 17, wherein the sensor is disposed adjacent the channel opposite the light source to detect a shadow of the particulate in the flow of fluid.

20. The sensing system according to claim 17, wherein the statistical analysis includes a real-time calculation of at least one of a running mean of the data, a standard deviation of the data, a variance of the data, a rise and fall slope of the data, a peak height of the data, and a peak height consistency between a rise and a fall of the data.

21. The method according to claim 1, wherein the transient fluid is jet fuel.

22. The method according to claim 10, wherein the transient fluid is jet fuel.

23. The system according to claim 17, wherein the transient fluid is jet fuel.

* * * * *